United States Patent [19]

Barton et al.

[11] 4,187,853

[45] Feb. 12, 1980

[54] ELECTRODE IMPLANTING APPARATUS WITH OPTIMUM LOCATION PROBE

[76] Inventors: Steven A. Barton, 401 S. Brazosport Blvd., Freeport, Tex. 77541; Sidney M. Barbanel, 2265 River Valley Dr., West Columbia, Tex. 77486

[21] Appl. No.: 957,916

[22] Filed: Nov. 6, 1978

[51] Int. Cl.² ............................................. A61N 1/04
[52] U.S. Cl. ............................. 128/419 PT; 128/783
[58] Field of Search ............ 128/419 P, 419 PT, 783, 128/784, 785

[56] References Cited

U.S. PATENT DOCUMENTS

| | | | |
|---|---|---|---|
| 4,026,301 | 5/1977 | Friedman et al. | 128/785 |
| 4,044,774 | 8/1977 | Corbin et al. | 128/784 |

Primary Examiner—William E. Kamm
Attorney, Agent, or Firm—Jones, Thomas & Askew

[57] ABSTRACT

Apparatus for implanting an electrode at an optimum location. The apparatus comprises an elongate body having two longitudinal shafts therein. A slot in the tip of the body temporarily secures the electrode to the tip. A probe in the second shaft may be extended from the tip and adjacent the electrode to thereby locate the optimum location for implantation of the electrode. The probe may thus be retracted within the second shaft for implanting of the electrode. After implantation of the electrode, a rod in the first shaft may then be extended into the slot to dislodge the electrode from the tip of the body.

6 Claims, 5 Drawing Figures

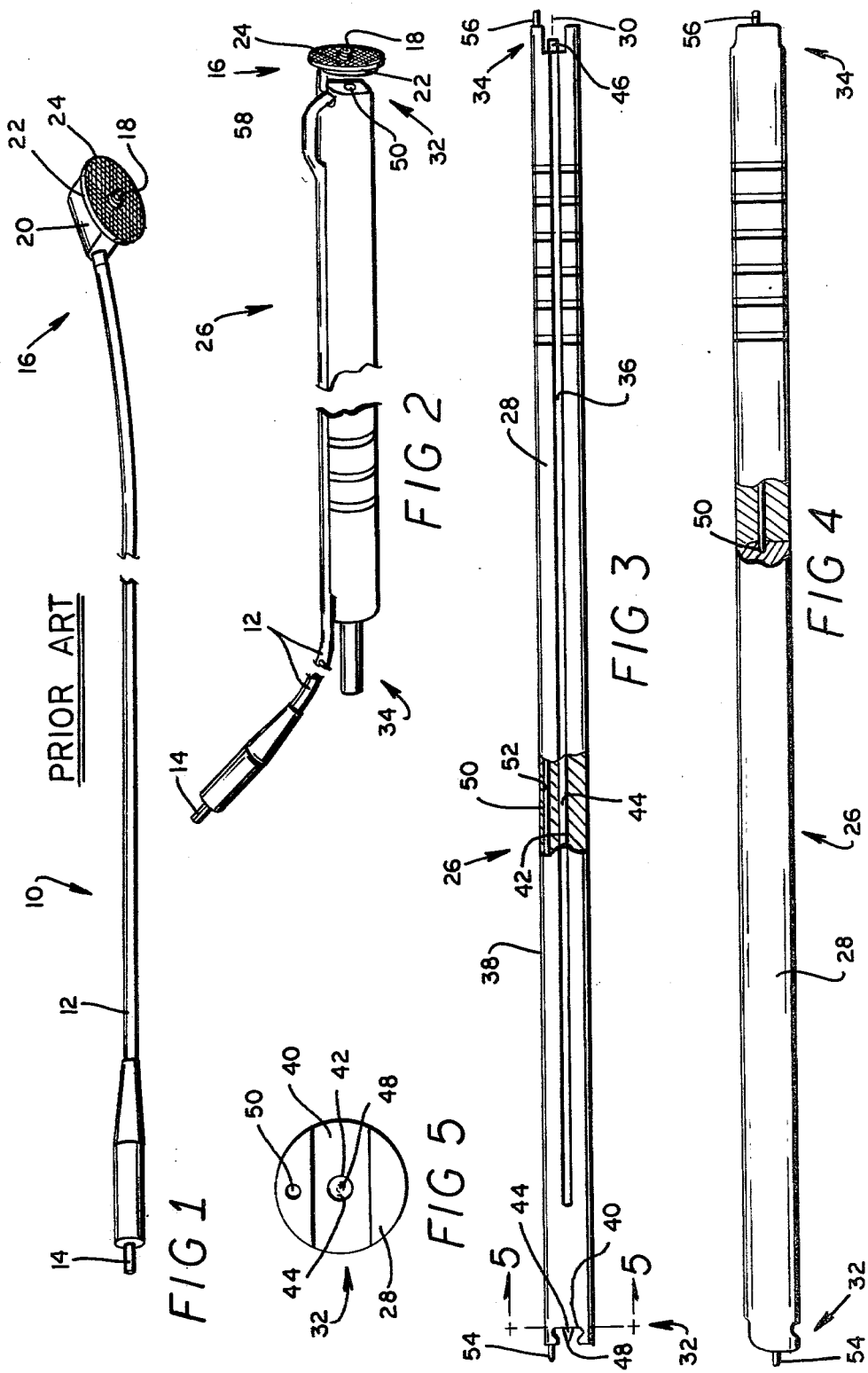

ELECTRODE IMPLANTING APPARATUS WITH OPTIMUM LOCATION PROBE

TECHNICAL FIELD

The present invention relates in general to apparatus for implanting an electrode in body tissue and in particular to apparatus for implanting an electrode at an optimum location for electrical stimulation of the body tissue.

BACKGROUND OF THE INVENTION

Pacemakers or other tissue stimulation devices generally operate to provide an electrical signal which is applied to certain body tissue so as to stimulate or otherwise affect the operation of an organ of the body. The actual stimulation signals are typically generated by a pacemaker or other apparatus which may be surgically implanted within the body, but not in direct contact with the heart or other organ to be regulated, and suitable electrical leads must then be provided to supply the signals from the electronic device to the particular organ of the body. Stimulation of the organ is typically accomplished by implanting or otherwise contacting the organ with an electrode attached to the electrical leads.

Stimulation electrodes are generally available in a variety of shapes and sizes. One such electrode is disclosed in U.S. Pat. No. 3,737,579 (hereby incorporated by reference). The electrode comprises a rigid helix adapted for attachment to body tissue and an insulated conductor attached at its one end to the helix and its other end being adpated for attachment to a power source. The electrode is attached to body tissue by screwing the helix into the body tissue. A device for facilitating the attachment of the electrode is also disclosed. The device comprises a substantially cylindrical-shaped tool having a slot in one end for holding the helical end of the electrode. A groove which extends substantially the entire length of the tool engages and holds the insulated conductor. The helix may be screwed into body tissue by rotating the tool about its longitudinal axis. The helical end of the electrode and the insulated conductor are then separated from the tool.

Separation of the helical end of the electrode from the slot without pulling the helix out of the body tissue or otherwise injuring the body tissue is often difficult. Therefore, it has also been known to provide a longitudinal bore in the attachment device of U.S. Pat. No. 3,737,579. The bore has a rod slidably disposed therein. The rod may be selectively extended to free the electrode from engagement with the slot to avoid damage to tissue in which the electrode is implanted which might otherwise occur if the electrode had to be pulled free from the slot.

A disadvantage of these prior electrodes and electrode implanting devices is that the electrode must be actually implanted in the tissue to determine the effect of stimulation on that particular area of tissue. If the desired effect is not achieved, the electrode must be removed and reimplanted. This procedure often causes undesirable damage to delicate tissue.

SUMMARY OF THE INVENTION

Generally, the present invention relates to a device for implanting an electrode at an optimum location for electrical stimulation of body tissue. More particularly the present invention comprises an elongate body having a tip at one end thereof. The tip of the body has a slot for temporarily securing an implantable electrode to the tip of the body. The body has two shafts therein. One of the shafts is adapted for accepting an elongate member. The other shaft is adapted for accepting an electrically conductive probe. When the probe is extended from the shaft, the probe projects from the tip of the body at a point adjacent the electrode secured to the tip of the body. The probe permits test stimulation of body tissue adjacent the electrode without actual implantation of the electrode. When a suitable site for implantation is located with the probe, the probe may be retracted into the shaft and the electrode implanted. Once the electrode is implanted the elongate member may be extended from its shaft, thereby dislodging the electrode from the tip of the body.

Accordingly, it is an object of the present invention to provide an improved electrode implanting device.

Another object of the present invention is to provide a device for implanting a stimulating electrode in body tissue which permits test stimulation of body tissue adjacent the electrode before its implantation to thereby permit selection of an optimum location for electrode implantation.

These and other objects, features and advantages of the present invention will become apparent from a review of the following detailed description of the disclosed embodiment and the appended drawing and claims.

BRIEF DESCRIPTION OF THE DRAWING

FIG. 1 is a pictorial view of an electrode of the type disclosed in U.S. Pat. No. 3,737,579.

FIG. 2 is a pictorial view of a disclosed embodiment of the apparatus of the present invention having the electrode and conducting lead shown in FIG. 1 attached thereto.

FIG. 3 is a partially sectioned side view of the apparatus shown in FIG. 2, with the electrode and conducting lead omitted to show the structure of the apparatus more clearly.

FIG. 4 is a partially broken-away top view of the apparatus shown in FIG. 3.

FIG. 5 is a cross-sectional view taken along the line 5—5 of the apparatus shown in FIG. 3.

DETAILED DESCRIPTION OF THE DISCLOSED EMBODIMENT

Referring to the drawing in which like numbers indicate like elements, it will be seen that there is a stimulation electrode device 10 of the type disclosed in U.S. Pat. No. 3,737,579. The electrode device 10 generally comprises lead 12 having an electric conductor therein, a connector tip 14 at one end of the lead for connection to a power supply or stimulator apparatus, such as a pacemaker or the like, and an electrode 16 connected to the other end of the lead. The electrode 16 comprises a rigid corkscrew-like coil 18 connected at a right angle to the electric conductor within the lead 12. The connection between the coil 18 and the electric conductor in the lead 12 is enclosed in a boot 20 of the general shape shown in FIG. 1. The boot is designed to mate with the tip of a tool to facilitate implantation of the coil 18 in body tissue as will be described in more detail hereinbelow. The coil 18 extends outwardly from the boot 20 and passes through a flange 22 of the boot and through a circular sheet of netting 24 attached to the flange. The netting 24 functions to enhance fibrotic growth to facilitate attachment of the electrode 16 to the body tissue after implantation.

Referring more particularly to FIGS. 2–5, it will be seen that there is an electrode implantation apparatus 26 for use in implanting an electrode of the type shown in FIG. 1 in body tissue. The apparatus 26 generally comprises an elongate, generally cylindrical-shaped body 28 having an imaginary longitudinal axis 30, a tip 32 for temporarily securing an electrode, and an end 34. A groove 36 formed in the surface 38 of the body 28, lying in a plane substantially parallel to the axis 30, extends from the end 34 of the body substantially the entire length of the body to a point short of the tip 32 of the body. The groove 36 is adapted for receiving and securely engaging at least a portion of the length of the lead 12 of the electrode device 10.

Formed in the tip 32 of the body 28 is a slot 40 substantially aligned at a right angle with the groove 36. The slot 40 is shaped so as to be adapted to substantially conform to and securely engage the boot 20 of the electrode 16. The edge defined by the tip 32 is rounded in order to prevent severe damage to subcutaneous tissue when the implanting apparatus 26 is used for surgically implanting an electrode.

Extending the entire length of the body 28 from the end 34 to the slot 40, substantially parallel to the axis 30, is a first axial opening or shaft 42. The shaft 42 is adapted for accepting a rod 44 therein to thereby permit sliding, reciprocating motion of the rod within the shaft. The rod 44 is generally of a length slightly greater than the length of the body 28 so that the tail 46 of the rod will project outwardly beyond the end 34 of the body when the tip 48 of the rod is retracted into the shaft just slightly inwardly from the slot 40 in the end 32 of the body.

Extending the entire length of the body 28 from the end 34 to the tip 32, substantially parallel to the axis 30 and spaced slightly radially outwardly from the first shaft 42, is a second shaft 50. The second shaft 50 is adapted for accepting a probe 52 therein to thereby permit sliding reciprocating motion of the probe within the shaft. The probe 52 is generally of a length slightly greater than the length of the body so that the point 54 of the probe may extend beyond the tip 32 of the body 28 with the tail 56 of the probe extending beyond the end 34 of the body 28. The probe is made of an electrically conductive material, and the tail 56 of the probe may be temporarily connected to the same or a separate stimulating device to which the electrode will be connected once implanted in the body tissue, or to a testing apparatus for evaluating the pacemaking threshold of a tissue site contacted by the probe.

The normal operation of the electrode implanting apparatus 26 is as follows. The rod 44 and the probe 52 are initially in a retracted position so that the tip 48 of the rod does not project into the slot 40 and the point 54 of the probe does not extend outwardly from the tip 32 of the body 28. The boot 20 of the electrode 16 is inserted into the slot 40 so that the electrode is securely held in the slot. The lead 12 is then inserted in the groove 36 leaving a small loop 58 (FIG. 2) of the lead extending outwardly from the body 28. The end of the lead 12 having the connector tip 14 is unconnected to a pacemaker or other apparatus at this time. In this position the coil 18 is in axial alignment with the longitudinal axis 30 of the body 28. The electrode 16 is then in position to be implanted in body tissue.

Before implantation of the electrode 16, the probe 52 is extended from the tip 32 by sliding the probe in the second shaft 50 in a direction toward the tip. The probe 52 is extended to a position so that the point 54 of the probe projects outwardly beyond the point of the coil 18. It should be understood that the placement of the second shaft 50 within the body 28 should be done in such a manner that the probe 54, when in its extended position, is as close to the coil 18 as possible while still providing sufficient clearance for the probe to clear the boot 20, flange 22, and the coil when the probe is extended and retracted. It will therefore be appreciated by those skilled in the art that when the probe 52 is in its extended position the point 54 is very close to the point where the coil 18 will be implanted.

The tail 56 of the probe 52 is then connected, for example, to suitable testing apparatus which simulates the operation of the pacemaker which is to be ultimately implanted in the body. The apparatus 26 is then manipulated by the surgeon to place the point 54 of the probe 52 in contact with various portions of the tissue to be stimulated. Since the probe 52 is connected to testing apparatus, it is possible to test the reaction of the tissue to stimulation before actual implantation of the electrode 16. In this manner, the probe 52 may be moved to various positions on the tissue in order to select the optimum site for implantation of the electrode.

Once the optimum site for implantation has been located, the point 54 of the probe 52 is retracted within the tip 32 by sliding the probe within the second shaft 50 in a direction toward the end 34 of the body 28. Then, without substantially moving the implanting apparatus 26 from the site selected, the point of the coil 18 is contacted to the tissue, and the body 28 is rotated in a direction shown by the arrow 60 (FIG. 2) to thereby screw the coil 18 into the body tissue. The body 28 is rotated until the coil 18 is firmly screwed into the tissue and until the netting 24 firmly contacts the outer surface of the tissue.

When the electrode 16 is thusly securely implanted in the tissue, the electrode 16 is dislodged from its attachment to the tip 32 of the body 28 by extending the rod 44 into the slot 40. The rod 44 may be extended by sliding the rod in the shaft 42 in a direction toward the tip 32. The rod 44 is extended into the slot 40 until the tip 48 of the rod contacts the boot 20 of the electrode 16. The rod 44 is then extended an additional amount so as to disengage the boot 20 from the slot 40, thereby freeing the electrode 16 from the tip 32 of the body 28. It will be appreciated by those skilled in the art that by so dislodging the electrode from the tip 32 of the body 28, damage to tissue in which the electrode is implanted, which might otherwise result in attempting to free the electrode from the tip, is reduced or prevented.

When the electrode 16 is freed from the tip 32 as described above, the lead 12 is removed from the groove 36. The connector tip 14 is then ready to be connected to the desired power source, stimulator, or the like, to be implanted under the skin or otherwise.

Although the present invention has been described as being used to insert electrodes of the type disclosed in U.S. Pat. No. 3,737,579, it is specifically contemplated that the present invention may be used to insert other electrodes of similar design. For example, the slot 40 may be altered in size and/or shape to accommodate screw-type electrodes of different shapes and configurations.

It should be understood, of course, that the foregoing relates only to a preferred embodiment of the present invention and that numerous modifications or alterations may be made therein without departing from the spirit and the scope of the invention as set forth in the appended claims.

We claim:

1. Apparatus for implanting an electrode, said apparatus comprising:
   an elongate body having a tip;
   means for temporarily securing said electrode to said tip;
   means operatively associated with said body for contacting body tissue adjacent said electrode with a signal probe while said electrode is temporarily secured to said tip; and
   means operatively associated with said body for selectably dislodging said electrode from said tip.

2. Apparatus of claim 1, wherein said securing means comprises a slot in said tip of said body, said tip accommodating said electrode to thereby temporarily secure said electrode in said slot.

3. Apparatus of claim 1, wherein said contacting means comprises a longitudinal shaft in said body, said shaft accommodating a conductive signal probe for reciprocating motion therein.

4. Apparatus of claim 1, wherein said dislodging means comprises:
   a rod; and
   a longitudinal shaft in said body, said shaft accommodating said rod for reciprocating motion therein.

5. Apparatus for implanting an electrode, said apparatus comprising:
   an elongate body having a tip;
   means for temporarily securing said electrode to said tip of said body;
   a first shaft in said body;
   an elongated member accommodated in said first shaft for reciprocal movement, wherein said rod has a retracted position whereby said electrode remains temporarily secured to said tip and wherein said rod has an extended position whereby said electrode is dislodged from said tip;
   a second shaft in said body; and
   a probe accommodated in said second shaft for reciprocating motion of said probe, wherein said probe has an extended position for engaging body tissue adjacent said tip and a retracted position, and wherein said probe may be extended and retracted while said electrode is temporarily secured to said tip.

6. Apparatus as in claim 5, wherein said probe is electrically conductive and has a portion which extends from said body for connection to a suitable signal means while said probe is extended from said body.

* * * * *